US010627383B2

(12) United States Patent
Tepper et al.

(10) Patent No.: US 10,627,383 B2
(45) Date of Patent: Apr. 21, 2020

(54) METHOD AND APPARATUS FOR MEASURING TRACE LEVELS OF FLUORESCENT MINERALS IN WATER

(71) Applicant: VIRGINIA COMMONWEALTH UNIVERSITY, Richmond, VA (US)

(72) Inventors: Gary Tepper, Richmond, VA (US); Brandon Dodd, Richmond, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 0 days.

(21) Appl. No.: 16/090,908

(22) PCT Filed: Apr. 21, 2017

(86) PCT No.: PCT/US2017/028719
§ 371 (c)(1),
(2) Date: Oct. 3, 2018

(87) PCT Pub. No.: WO2017/184914
PCT Pub. Date: Oct. 26, 2017

(65) Prior Publication Data
US 2019/0120808 A1     Apr. 25, 2019

Related U.S. Application Data
(60) Provisional application No. 62/325,699, filed on Apr. 21, 2016.

(51) Int. Cl.
*G01N 33/18* (2006.01)
*G01N 21/64* (2006.01)

(52) U.S. Cl.
CPC ....... *G01N 33/1813* (2013.01); *G01N 21/645* (2013.01)

(58) Field of Classification Search
CPC .... G01N 21/64; G01N 21/643; G01N 21/645; G01N 33/18; G01N 33/1813
See application file for complete search history.

(56) References Cited

U.S. PATENT DOCUMENTS

| 4,236,071 A * | 11/1980 | Chimenti | G01N 21/64 204/157.22 |
| 4,239,964 A * | 12/1980 | Robbins | G01N 21/6408 250/255 |
| 6,336,957 B1 | 1/2002 | Tsymerman | |
| 2001/0018209 A1 | 8/2001 | Asada et al. | |

(Continued)

OTHER PUBLICATIONS

Sill et al, "Fluorescence Test for Uranium in Aqueous Solution", Anal. Chem, 1947, 19 (9) pp. 646-651 (Year: 1947).*

(Continued)

*Primary Examiner* — David E Smith
(74) *Attorney, Agent, or Firm* — W&C IP (57) ABSTRACT

Methods and devices to rapidly detect trace levels of water soluble fluorescent mineral species such as uranium in aqueous fluids (e.g. water) are provided. The methods and devices involve sequestration of cationic forms of the water soluble fluorescent mineral species (e.g. the uranium oxycation uranyl, $UO_2^{2+}$) via pressurized fluid flow through a porous silica gel medium, to enhance natural fluorescence and increase the speed of detection.

12 Claims, 8 Drawing Sheets

(56) References Cited

U.S. PATENT DOCUMENTS

2009/0215646 A1* 8/2009 Anslyn ............ G01N 33/54313
                                                                 506/12
2013/0177991 A1     7/2013 Tang et al.

OTHER PUBLICATIONS

Lopez et al, "Uranyl Photophysics on Colloidal Silica: an Alternative Luminescence-Enhancing Meduium for Uranyl Assay", Analyst, Jul. 1996, vol. 121, pp. 905-908 (Year: 1996).*

Lopez (Lopez et al, "Uranyl Photophysics on Colloidal Silica: an Alternative Luminescence-Enhancing Medium for Uranyl Assay", Analyst, Jul. 1996, vol. 121 pp. 905-908) (Year: 1996).*

Sill et al., Fluorescence Test for Uranium in Aqueous Solution, Anal. Chem., 1947, 19 (9) pp. 646-651.

Lopez et al., Uranyl Photophysics on Colloidal Silica: an Alternative Luminescence-enhancing Medium for Uranyl Assay, Analyst, Jul. 1996, vol. 121, pp. 905-908.

* cited by examiner

METHOD AND APPARATUS FOR MEASURING TRACE LEVELS OF FLUORESCENT MINERALS IN WATER

CROSS-REFERENCE TO RELATED APPLICATIONS

This application claims benefit of U.S. provisional application 62/325,699, filed Apr. 21, 2016, the complete contents of which is hereby incorporated by reference.

BACKGROUND OF THE INVENTION

Field of the Invention

The invention generally relates methods and devices to rapidly detect trace levels of water soluble fluorescent mineral species in aqueous samples. In particular, the methods and devices involve sequestration of fluorescent cationic forms of the water soluble mineral species via pressurized fluid flow through a porous silica gel medium, which enhances natural fluorescence and increases the speed of detection. In some aspects, the water soluble fluorescent species is uranyl, the oxycation of uranium.

Background

Uranium is a heavy, naturally occurring radioactive element. Elevated concentrations of uranium in water and soil can be linked to activities such as uranium mining, nuclear fuel preparation and disposal (1-3). Monitoring the concentration of uranium in the environment is of interest to organizations involved in activities such as national security, non-proliferation, water quality, and environmental impact studies (4, 5). Uranium can be detected in several ways, but the most common method is measuring the high-energy radioactive decay products. However, at low concentration levels in soil or water, uranium radioactivity signals are weak and attenuated and, therefore, difficult to measure outside of a laboratory.

Uranium in nature is most commonly found in an oxidized ionic form known as uranyl, with oxidation state +6 and chemical formula $UO_2^{2+}$ (6, 7). The uranyl ion is water soluble and has been known for its distinct green fluorescent emission for over 150 years (8). The uranyl optical emission signature can have as many as six peaks at wavelengths ranging from 345-600 nm, depending on factors such as pH and temperature (9). Each of these peaks is due to the vibrational modes of the two smaller oxygen atoms vibrating around the much larger uranium atom (1, 2, 10). The fluorescence emitted from the uranyl ion has long been used as a method for determining the presence and concentration of uranyl in water (11-13). However, water molecules quench the optical emission making detection at trace concentration levels challenging (8). Multiple methods have been used to enhance the fluorescence of uranyl in water e.g. phosphoric acid, low temperatures, colloidal silica, etc. (7, 9, 11, 12, 13).

Studies of silica in the presence of metal ions have shown that silica has a high adsorption capacity and selectivity, especially when used with uranyl (15). The selectivity towards uranyl ions is caused by the negatively charged sites on the silica surface, to which the uranyl ions attach (11). Two important parameters need to be considered when using silica to enhance uranyl fluorescence: the kinetics of the adsorption process and the equilibrium capacity (15). The equilibrium capacity refers to the total number of silica surface sites available to adsorb a uranyl ion, while the kinetics of adsorption is the time required to fill those sites. The kinetics has been studied for various solutions and with different methods such as in a static or stirred fluid (15). The tests show that in a static or stirred fluid, the time required for uranyl to reach equilibrium capacity can be on the order of hours (15), which is much too slow for most measurement applications.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

The invention provides methods and devices to rapidly detect trace levels of water soluble fluorescent mineral species in aqueous samples. According to the invention, cationic forms of the water soluble fluorescent mineral species are directed through a porous silica gel medium under pressure. The cationic species bind to the negatively charged silica gel, thereby enhancing their natural fluorescence. The fluorescent enhancement, together with pressurized flow, greatly increases the speed of detection of the fluorescent species.

Accordingly, the present disclosure describes methods and apparatuses for rapidly (e.g. on the order of seconds) detecting even very low levels of water soluble fluorescent species in aqueous fluids such as water. As described herein, fluid flow through a nanoporous silica gel medium is used to both enhance fluorescence and to increase the speed of fluorescence detection. In particular, the present disclosure describes the role of fluid velocity on the kinetics of adsorption in nanoporous silica gel of the exemplary water soluble fluorescent species uranyl, and shows that the kinetics can be greatly enhanced under the appropriate conditions.

The invention also provides portable, hand-held devices to detect and measure water soluble fluorescent species such as uranyl (e.g. uranyl oxycations) in aqueous solutions. The device pumps an aqueous fluid potentially containing dissolved e.g. uranyl through a silica gel solid state porous media. If cationic form of the water soluble fluorescent species is present in the sample, it adsorbs onto the silica gel surface. The interaction between the cations and the silica gel produces a strong enhancement in natural fluorescence. The device comprises a compact UV excitation source and a photodetector to measure the fluorescence of species adsorbed within the silica gel porous media. Optical filters may also (optionally) be used to enhance the signal to noise ratio. Trace levels of e.g. uranyl in water can be detected and measured using this apparatus. Furthermore, the detection speed is improved by ~3 orders of magnitude by using a pump to force the liquid sample through the porous silica media at flow rates above a critical value. The invention makes it possible to measure very low levels of water soluble fluorescent mineral species in water in seconds using a simple hand-held device that can be powered by a battery, providing a rapid and simple method to measure and quantify uranium in water. The invention has broad commercial applications in defense, security and environmental monitoring.

It is an object of this invention to provide methods of detecting water soluble fluorescent mineral species in an aqueous sample, comprising i) directing under pressure the aqueous sample through a solid state porous silica gel; ii) irradiating the solid state porous silica gel with UV light during the step of directing; iii) detecting fluorescence emitted from the water soluble fluorescent mineral species bound to the solid state porous silica gel during the step of irradiating, iv) comparing a level of fluorescence detected in step iii) with at least one negative control value; and v) confirming or indicating that the aqueous sample contains the water soluble fluorescent mineral species when the level of fluorescence detected in step iii) exceeds that of the at least one negative control value. In some aspects, the negative control value is a level of fluorescence emitted when a control aqueous sample that does not contain the water soluble fluorescent mineral species is directed over a control solid state porous silica gel. In some aspects, the UV light has a wavelength ranging from 250 to 400 nm. In other aspects, the fluorescence has a wavelength ranging from 345 to 600 nm. In additional aspects, the methods further comprise a step of enhancing a signal to noise ratio of the fluorescence detected in step iii) using an optical filter. In some aspects, the water soluble fluorescent mineral species is uranyl; and in further aspects, the aqueous sample is directed through the solid state porous silica gel at a flow velocity greater than or equal to 0.36 cm/sec. In yet further aspects, the methods comprise a step of washing the solid state porous silica gel and repeating steps i)-v).

The invention also provides devices for detecting uranyl in an aqueous sample. The devices comprise: a chamber for containing solid state porous silica gel; a directing device which directs the aqueous sample through the solid state porous silica gel in the chamber; an ultraviolet (UV) excitation source; and a fluorometer; wherein the device is configured to: i) permit UV light from the UV excitation source to penetrate the solid state porous silica gel, and ii) permit fluorescence emitted from the silica gel to reach the fluorometer. In some aspects, the device is a portable, hand held device. In other aspects, the device comprises one or more optical filters. In additional aspects, the directing device is selected from a pump, a propeller and a suction port. In yet further aspects, the device directs the aqueous sample through the solid state porous silica gel at a flow velocity greater than or equal to 0.36 cm/sec.

DETAILED DESCRIPTION

Provided herein are methods and devices for detecting water soluble fluorescent species (e.g. fluorescent mineral species) in aqueous samples, e.g. in water. According to the methods, what is detected is a cationic form of the water soluble fluorescent species. For example, for uranium, the uranium oxycation uranyl ($UO_2^{2+}$) is detected. An aqueous sample that is suspected of containing (e.g. being contaminated with) e.g. uranium is pumped through a silica gel solid state porous medium under pressure. If water soluble fluorescent cations are present in the sample, they bind to negatively charged groups in the silica, and binding causes a strong enhancement of natural fluorescence. Detection of an increase in fluorescence is therefore confirmation that the sample contains the water soluble fluorescent species. In some aspects, adjusting the flow rate of the sample to be at or above a determined value advantageously makes it possible to detect such increases in fluorescence on a time scale of seconds. For example, for uranium, the optimum velocity of flow is at or above about 0.36 cm/sec. Thus, the flow is fed into the silica under pressure and the sample is not wicked, dripped or gravity fed into the silica. Rather, it is directed into the silica gel at a selected velocity or range of velocities discussed below, all of which are substantially greater than wicking, dripping, or gravity. This technology is well-suited for incorporation into portable, handheld devices for detecting trace levels of water soluble fluorescent species such as uranium, e.g. in water.

"Fluorescence" refers to the emission of light by a substance that has absorbed light or other electromagnetic radiation, e.g. UV light. It is a form of luminescence. In most cases, the emitted light has a longer wavelength, and therefore lower energy, than the absorbed radiation. For example, fluorescence occurs when the absorbed radiation is in the ultraviolet region of the spectrum, and thus invisible to the human eye, while the emitted light is in the visible region, which gives the fluorescent substance a distinct color that can only be seen when exposed to UV light.

By "silica gel" we mean a granular, vitreous, nanoporous form of silicon dioxide made synthetically from sodium silicate. Silica gel contains a nanoporous silica micro-structure, suspended inside a liquid. When dried, the silica gel may be referred to as "silica xerogel", and the two phrases may be used interchangeably. Silica is a naturally occurring mineral that is purified and processed into both granular or beaded form, and having a strong affinity for water molecules. The "porosity" of a silica gel as used herein refers to the open porosity of the gel, i.e. the fraction of volume of the interconnected porous network that is accessible to fluid flowing through the gel.

Exemplary silica gels suitable for use in the practice of the invention include but are not limited to: those with a particle size (μm) ranging from about 50 to about 400, e.g. about 50, 60, 70, 80, 90, 100, 120, 130, 140, 150, 160, 170, 180, 190, 200, 210, 220, 230, 240, 250, 260, 270, 280, 290, 300, 310, 320, 330, 340, 350, 360, 370, 380, 390 or 400; and with a surface area ($m^2$/g) of from about 300-800, e.g. about 300, 350, 400, 450, 500, 550 600, 650, 700, 750 or 800; and a pore size (Å) of from about 10 to 120, e.g. about 10, 20, 30, 40, 50, 60, 70, 80, 90, 100 or 120. Those of skill in the art will recognize that an optimal silica gel is selected based on instrument performance parameters such as flow rate and photo detector settings. Fluorescent output and equilibrium capacity are also taken into consideration. Surprisingly, the flow rate of the sample through the silica in some embodiments may be of significance, with optimal results e.g. for uranium being obtained at a flow rate at or above about 0.36 cm/sec. Thus, for a mineral species that is detected, the flow rate is generally maintained at or about 0.1. 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.55, 3.6, 3.7, 3.8, 3.9, 4.0, 4.1, 4.2, 4.3, 4.4, 4.5, 4.6, 4.7, 4.8, 4.9 or 5.0 cm/sec or more. In some aspects, the flow rate is from about 0.3 cm/sec to about 10 cm/sec, and is preferably at or above 0.36 cm/sec (e.g. for uranyl). In general, the faster portion of this range of flow rates is used to reduce the response time for samples that require larger volumes of solution to be moved through the silica gel to produce a proper detectable signal e.g. when the concentration of e.g. uranyl in the sample is very low, for example, less than about 100, 90, 80, 70, 60, 50, 40, 30, 20 or 10 parts per trillion. In some aspects, the concentration of e.g. uranyl in the sample is about 10 ppt or even less, e.g. 9, 8, 7, 6, or 5 ppt. The optimal flow rate and/or range of flow rates can be determined and/or adjusted to a suitable level by selecting an appropriately sized pump and/or power supply.

In some aspects, the silica gel that is used is not functionalized with chelating or detecting groups, e.g. is not chemically modified to include other agents that bind water soluble fluorescent species.

On one aspect, the water soluble fluorescent mineral species that is detected is uranium, that is, the oxycation of uranium, uranyl. However, other fluorescent mineral fluorophores are also detectable using the methods and devices described herein. In general, such species are capable of absorbing light energy in the UV range (e.g. UV excitation <380 nm) and reemit the energy at a longer wavelength, e.g. in the fluorescent range. Exemplary fluorescence minerals that may be detected include but are not limited to: divalent manganese (which emits red or orange fluorescence in the range of 590 nm-700 nm); trivalent chromium (which emits red fluorescence in the range of 620 nm-750 nm); divalent europium (which emits blue fluorescence in the range of 450 nm-495 nm); trivalent lanthanides such as terbium and dysprosium (which emit yellow fluorescence in the range of 570 nm-590 nm); powellite (calcium molybdate, (which emits yellow fluorescence in the range of 570 nm-590 nm); scheelite (calcium tungstate, which emits blue fluorescence in the range of 450 nm-495 nm); and sphalerite (zinc sulfide, which fluoresces and phosphoresces in a range of colors in the range of 450 nm-650 nm). Further, in some aspects, the species that is detected is not a water soluble mineral or cation of a water soluble mineral per se, but is for example, a species that is only sparingly soluble or insoluble in aqueous solution but which can nevertheless form an emulsion or suspension and be detected by the methods and devices described herein. Examples of this class of species include but is not limited to crude oil (petroleum, or components thereof) which fluoresces in a range of colors (emission: 570 nm-650 nm). In such cases, it may or may not be a cationic form of the fluorescent material that binds to or is retained by the silica gel, i.e. a non-cationic form may be sequestered by the silica such one or more uncharged or hydrophobic components.

The invention provides devices/apparatuses for carrying out the methods described herein. In some aspects, the devices are hand-held devices, e.g. devices that can be held by the user and actuated using one or both hands. In some aspects, the devices are portable, i.e. they can be operated without accessing an external electrical power source. In general, the power source of such portable devices is one or more batteries. However, devices which require an external electrical power source (AC or DC) are also encompassed, as are devices in which the use of an external power source is optional (i.e. both a battery and a means of connecting to an external power source are present in the device). In some aspects, the device is solar powered, e.g. comprises a solar battery such as a rechargeable solar battery. Various handheld, portable devices for liquid analysis are known, albeit not for detecting trace levels of water soluble fluorescent species. Examples of hand-held devices are described, for example, in published US patent applications 2015/0233817 and 20120156688; and issued U.S. Pat. Nos. 8,778,846 and 5,538,689, the complete contents of each of which is hereby incorporated by reference in entirety.

In some aspects, the device for detecting water soluble fluorescent species in an aqueous sample comprises: a reservoir for receiving and/or containing an aqueous sample; a chamber for containing solid state porous silica gel; a pump to pump the aqueous sample from the reservoir to and through the solid state porous silica gel in the chamber; an ultraviolet (UV) excitation source to emit one or more wavelengths suitable for interrogating cationic forms of water soluble fluorescent species bound to silica; and a fluorometer to receive and measure fluorescence emitted from the silica-bound cations, the device being configured to: i) permit UV light from the UV excitation source to penetrate the solid state porous silica gel in the chamber, and ii) permit fluorescence emitted from the cationic species bound to the silica gel to reach the fluorometer.

Generally, the reservoir is designed to receive an aqueous sample to be analyzed and thus has a first opening or port through which the sample is placed in the reservoir. The sample may be delivered to the reservoir and through the port by any suitable means, e.g. by pipetting, via a needle and syringe, or for larger samples directly pumping from the source. Alternatively, the reservoir may be detachable from the device and tillable, e.g. by dipping it into a water source to be sampled, or by otherwise placing the sample therein. The reservoir is then reconnected to the device by being snapped, slid, etc. or otherwise placed within a reservoir holder. The reservoir also comprises a second opening or port through which the sample passes when leaving the reservoir, e.g. to move toward the silica gel for analysis. Prior to placement in the reservoir, the samples may be pretreated, e.g. via filtration or centrifugation, to remove particulate matter or other materials that could otherwise interfere with handling and measuring, or by dilution or concentration, etc.

The sample is generally directed (e.g. pumped) from the reservoir toward the chamber that contains the silica gel via a mechanism such as a pump, a propeller, a suction port, etc. A pump is typically a micropump that is integrated internally into the device and is connected to both the reservoir and the chamber that contains the silica gel by conduits for the sample. The pump may be external to the reservoir, or may be submersible and located within the reservoir, or within the chamber that contains the silica gel. In some aspects, the pump is external to the device, and may, for example, be attachable thereto. The pump generally comprises or is electrically connected to an actuator to turn it on and off, and may be battery powered and/or solar powered, with an option to. Exemplary micropumps that may be employed include but are not limited to: microfluidic pumps, piezoelectric pumps, peristaltic pumps, etc., and the pump may be submersible.

In order to control, adjust and monitor the flow rate of the sample into and through the chamber, a flow meter can be present between the pump and the chamber, e.g. an inline flow meter within a sample conduit located between the pump and the chamber. In some aspects, the flow meter is a flowmeter with a valve that is suitable for changing or adjusting the flow rate of the sample through the conduit, such as a needle valve. As described above, an optimal flow rate is generally at least about 0.36 cm/sec. Exemplary flow meters and valves that may be employed to achieve such flow rates include but are not limited to: digital flow meter with an electronically controlled adjustment valve, flow meter with a manual adjustment valve, a flowmeter with a separate valve to adjust the flow rate, etc.

Generally, the chamber for containing the solid state porous silica gel is designed to receive the silica gel via direct loading through an opening that leads into the chamber, and is refillable with new silica gel (e.g. in the form of pourable beads, or preformed solid or semi-solid silica gel in any shape, e.g. a sheet, wafer or cylinder, etc. that snaps or slides or is otherwise insertable into the chamber and which can be removed from the chamber and disposed of (or washed and reused) after use. In other aspects, the chamber is designed to receive an insertable and removable carrier that contains the silica gel, such as a cartridge; a "tea bag" made of water permeable netting or webbing, a capsule the can be punctured to allow fluid to pass through, etc. The carrier may be refillable or may be prefilled and disposable.

The chamber itself may be water-impermeable except for a first opening through which a sample enters the chamber (e.g. from the pump via a valve) and a second opening through which a sample leaves the chamber. Further, an opening for inserting or placing the silica gel into the chamber and removing the gel after use can be present, and can be closeable so as to maintain the water-impermeability of the chamber after gel insertion and during use, e.g. closeable with a water tight seal.

The walls of the chamber (and/or cartridge) generally can comprise a window that permits passage of interrogating excitation wavelengths of light from a UV source into the chamber and into the silica gel therein. Cations adsorbed within the silica gel absorb the light and emit fluorescence. Emitted fluorescence leaves the chamber through a window and enters a fluorescence detector (fluorometer) where the amount of fluorescence is measured. Two separate windows may be present in the chamber, one for the entrance of light and one for emission, or a single window may serve for transmission of both the UV light and fluorescence. In addition, optical filters may be used.

The UV light that impinges on the silica gel is generally in the range of from about 250 to 400 nm, e.g. about 250, 255, 260, 265, 270, 275, 280, 285, 290, 295, 300, 305, 310, 315, 320, 325, 330, 335, 340, 345, 350, 355, 360, 365, 370, 375, 380, 385, 390, 395 or 400 nm. Exemplary UV wavelengths, which are used either alone or in combinations of two or more, include but are not limited to: 266, 280, 310, 325, 355 and 365 nm.

The fluorescence that is emitted from the e.g. uranyl oxycations is generally in the range of from about 345-600 nm, and the entire spectrum may be gathered and used for analysis, or one or more particular wavelengths may be monitored and measured, e.g. one or more of about 496, 518 or 540 nm.

Those of skill in the art are familiar with micro components that are readily commercially available and which may be used in the present devices. Examples include but are not limited to, for example: micro UV light sources such as UV light emitting diodes (LEDs), UV laser diodes, etc.; various microfluorometers or microspectrophotometers configured for fluorescence micro photo detectors etc.

After flowing through the silica gel in the chamber, in some aspects, the sample flows out of the chamber and back to the reservoir through a conduit. In this aspect, a single sample flows cyclically and continuously through the device for a period of time sufficient to insure that all or a majority of the e.g. uranyl cations in the sample have bound to the silica gel, e.g. for a range of at least 5 seconds to a few minutes as a maximum. This range of time is sufficient to measure high concentrations of e.g. uranyl (e.g. in the parts per million range) as well as very low concentrations (e.g. in the parts per billion or even parts per trillion range).

In other aspects, the sample does not cycle through the device multiple times but flows through the silica gel only once and is then channeled into a waste reservoir, or is evacuated from the device through a port, e.g. via a length of tubing, etc.

Figure 7A:
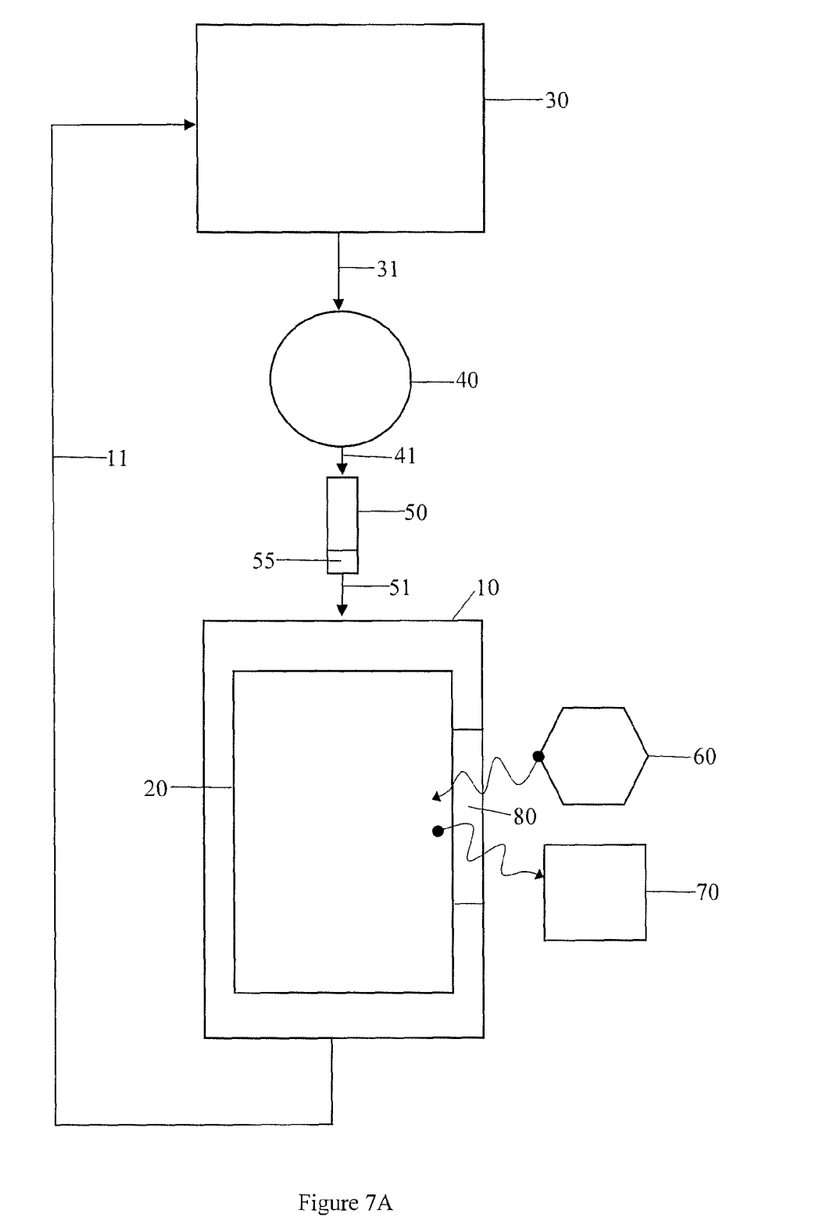
FIGS. 7A and B. Schematic representations of a device. A, device in which sample circulates; B, device in which sample makes a single pass.

A schematic drawing of an exemplary device is depicted in FIG. 7A. Shown are chamber 10 for containing silica gel 20. Reservoir 30 contains a sample to be assessed, the sample passing via conduit 31 to pump 40 (if pump 40 is not submersed within reservoir 30). The sample passes from pump 40 via conduit 41 to flow meter 50, which contains a valve 55. The sample passes into chamber 10 via conduit 51, and exits chamber 10 and proceeds back to reservoir 30 via conduit 11. While passing through silica gel 20 in chamber 10, UV light is transmitted form UV light source 60 through window 80 and into silica gel 20. Fluorescence emitted by e.g. uranyl cations sequestered in silica gel 20 leaves via window 80 and enters fluorometer 70, where it is detected and measured, e.g. quantified as to amount (wave amplitude) and identity (spectrum of the wavelengths that are present).

Figure 7B:
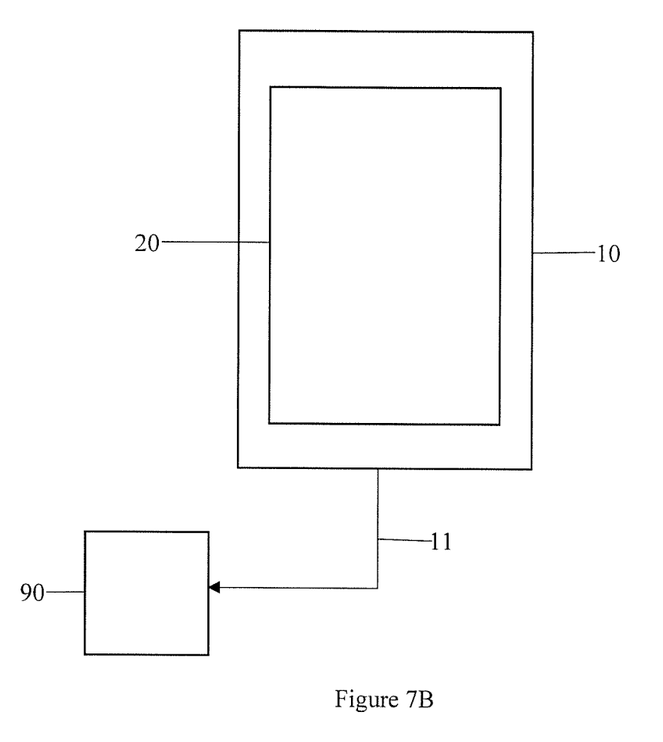

In an alternative aspect, conduit 11 does not lead back to reservoir 30 but rather connects to waste reservoir 90 (FIG. 7B) or to the environment (not shown), so that the sample makes a single pass through silica gel 20.

Generally, after the analysis of one sample, the silica gel is removed from the chamber and discarded, and new silica gel replaces the previous silica gel. However, in some aspects, the silica gel can be chemically washed and reused (e.g. by flowing water or buffer comprising no detectable fluorescent mineral cations through the device) until fluorescent mineral cations are dislodged from the silica gel and the fluorescence transmitted from the device is at background levels.

Data collected by the fluorometer is processed, e.g. by a microprocessor located in the device. Processing may include comparison of the fluorescence data with stored fluorescence data from control samples such as samples containing known amounts of e.g. uranyl, negative samples that do not contain detectable levels of e.g. uranyl, etc. The data is correlated with such control samples and the amount of e.g. uranyl cations adsorbed to the silica gel is calculated. Generally, the device is equipped with at least one display screen for displaying data. The displayed data may include, for example, the fluorescence spectra that are obtained, and/or multiple spectra obtained over time (e.g. taken at defined time intervals as a sample circulates through the device), and/or charts, graphs or tables which numerically depict the amount of fluorescent mineral cations present in one or more samples, etc. as well as information that identifies the sample, the silica gel characteristics/properties, parameters employed during data collection (e.g. flow rate), etc. Relevant information may be input by the user, and the microprocessor generally allows data manipulation by the user, e.g. retrieval of stored data (e.g. control data, results of previous analyses from a sample source that was obtained at an earlier point in time, etc.), comparison of various sample analyses, etc. The microprocessor generally is capable of sending data to and receiving data from a storage site, e.g. a cloud, another computer, etc.

The samples that are analyzed using the devices and methods described herein are generally aqueous fluid samples, which is defined as liquid solutions in which water is the principle solvent. Exemplary types of samples that can be analyzed or assessed using the methods and devices described herein include but are not limited to: drinking water; sea water; water from fresh water lakes, streams and rivers; effluent from nuclear reactors; water associated with nuclear weapons manufacturing, storage, use or destruction; water associated with or that might be affected by stored sources of uranium or other fluorescent minerals; rain water; runoff from deposits of uranium or other fluorescent minerals; glacial melt water; body fluids; and any other fluids that can come in contact with sources of minerals such as uranium. The samples that are assessed are generally aqueous (e.g. water) based liquids but the analysis of other types of samples is also encompassed. For example, liquid or filtrate decanted from solid samples that are extracted using water (e.g. soil, "wipes" from surfaces that are suspected or at risk of uranium contamination, etc.); or aqueous "washes" of hydrophobic samples such as hydrocarbons (e.g. oil, gasoline), etc. that cannot, or cannot readily, be analyzed directly in the device; and any other scenario in which the fluorescent material and/or cationic forms thereof is in or can be transferred to an aqueous solution from a source that cannot be analyzed directly using the present device. In some aspects, however, the sample may contain a fluorescent substance of interest that is only partially or sparingly soluble in aqueous solutions The invention also provides methods of measuring or detecting water soluble fluorescent species in aqueous samples. The methods include, for example, step i) directing (e.g. pumping, flowing, etc.) an aqueous sample through a solid state porous silica gel under pressure; ii) irradiating the solid state porous silica gel with UV light during the step of pumping; iii) detecting fluorescence emitted from cationic forms of the water soluble fluorescent species bound to the solid state porous silica gel during the step of irradiating, iv) comparing a level of fluorescence detected in step iii) with at least one negative control level of fluorescence and v) confirming or indicating that the aqueous sample contains water soluble fluorescent species when the level of fluorescence detected in step iii) exceeds that of the at least one negative control value. In some aspects, when the water soluble fluorescent species is uranyl, the sample is directed at a flow velocity greater than or equal to about 0.36 cm/sec. While generally the method is practiced by irradiating the sample during pumping, in some aspects, the pumping step is performed for a period of time ranging e.g. from about 5-10 seconds to about 5 minutes, before the sample is irradiated and the fluorescence is measured. Thus, the water soluble fluorescent cations are loaded onto the silica before the measurement is taken.

Those of skill in the art are well-acquainted with establishing suitable negative and positive controls. In some aspects, a suitable negative control level of fluorescence is the fluorescence emitted when a negative control sample comparable to the test sample (e.g. matched in terms of pH, solvent composition, etc. but containing e.g. no uranyl oxycations detectable by another established technique) is pumped through a comparable, matched solid state porous silica gel at the same velocity and under the same conditions (e.g. temperature, same UV excitation wavelengths, etc.), allowing a practitioner to conclude, confirm or indicate, by comparison, whether or not the experimental test sample contains e.g. uranium species.

In other aspects, suitable positive control levels of fluorescence include the level of fluorescence emitted when a positive control sample comparable to the test sample (e.g. matched in terms of pH, solvent composition, etc., but containing a known quantity of e.g. uranyl oxycations) is pumped through a comparable, matched solid state porous silica gel at the same velocity and under the same conditions (e.g. temperature, same UV excitation wavelengths, same length of time, etc.). A range of positive control samples containing a range of different amounts of e.g. uranyl oxycations may be used, permitting a practitioner to conclude, by comparison, whether or not the experimental test sample contains e.g. uranium species, and also the quantity, amount or level of e.g. uranium species present in the experimental test sample. Those of skill in the art will recognize that the same or similar procedures can be readily applied to establishing controls for other fluorescent species.

In some aspects of the method, the UV light that is used to irradiate has a wavelength ranging from e.g. about 280 to about 400, and the fluorescence that is detected (either a single wavelength, or multiple wavelengths of interest, or a full spectrum) has a wavelength ranging from 345 to 600 nm.

In further aspects of the method, the signal to noise ratio of the fluorescence is enhanced using an optical filter.

In general, excitation and fluorescence detection is carried out for a period of time of about 60 seconds or less, e.g. for less than about 60, 55, 50, 45, 40, 35, 30, 25, 20, 15, 10, or 5 seconds, or for even shorter periods of time, e.g. 1, 2, 3 or 4 seconds. Especially in aspects in which the sample is circulated through the silica gel continuously, measurements may be taken at timed intervals at least until a maximum of fluorescence signaling is detected, since more and more cations may bind to the silica gel with time.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLE

Experimental Methodology

Sample Preparation

Silica gel was purchased from Sigma-Aldrich and Acros Organics with nominal pore sizes ranging from 22 Å to 100 Å and particle sizes from 40 μm to 650 μm as reported by the manufacturer. The specific properties of each silica gel used in this study (referred to here as SG-1 through SG-5) are shown in Table 1.

TABLE 1

Physical properties of silica gel

| Item No. | Company | Pore Size (Å) | Particle size (μm) | Surface Area (m2/g) |
|---|---|---|---|---|
| SG-1 | Sigma-Aldrich | 22 | 75-650 | 800 |
| SG-2 | Sigma-Aldrich | 30 | 75-150 | 480 |
| SG-3 | Acros Organics | 40 | 40-60 | 750 |
| SG-4 | Acros Organics | 60 | 40-60 | 550 |
| SG-5 | Sigma-Aldrich | 100 | 63-200 | 300 |

Figure 1A:
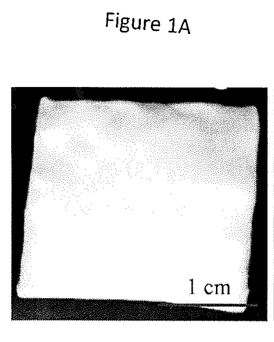
FIG. 1A-F. A) Silica-filled nylon bag; B) 20× optical image of the nylon mesh; C) optical image of SG-3; D) Scanning electron microscope (SEM) image of SG-1; E) SEM image of SG-3; and F) SEM image of SG-5.
Figure 1B:
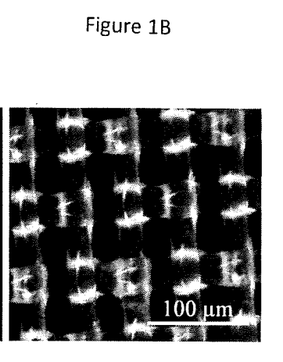
Figure 1C:
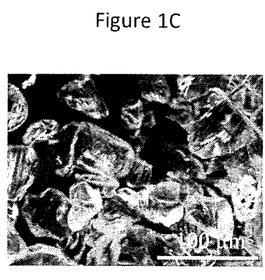
Figure 1D:
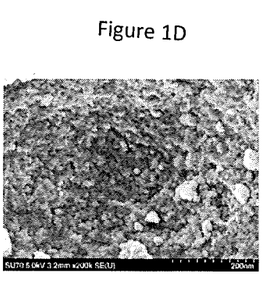
Figure 1E:
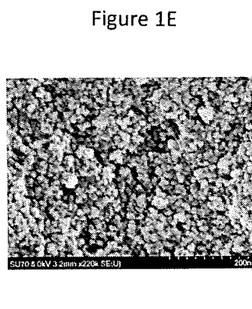
Figure 1F:
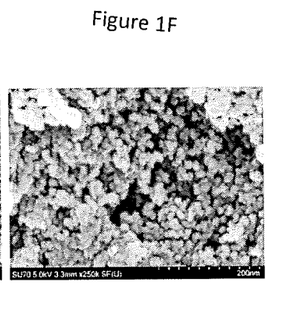

The silica gel particles were packed together in custom-made 1-inch square bags made of a monofilament nylon mesh with an opening size of 28 μm purchased from McMaster-Carr. The bags were made by melting the edges together with a small flame. Using a Fisher-Scientific accu-124 balance, 250 mg of silica was measured and transferred into each of the nylon bags, which were then sealed. A filled nylon bag and a 20× optical microscope image of the mesh pores are shown in FIGS. 1A and 1B. FIG. 1 also includes an optical image of SG-3 (FIG. 1C) and scanning electron microscope (SEM) images of SG-1, SG-3, and SG-5 (Figures D-F). It can be seen that silica gel particles comprise an assembly of bonded silica nanoparticles with open pores between the particles similar to a granular bed.

A 0.01 M aqueous uranyl solution was used in all of the experiments discussed in this Example and was prepared from a uranyl nitrate salt and 10 MΩ-cm pure deionized water.

Full Spectra Measurements

The florescence emission of the uranyl was performed using a QuantMaster™-3 Spectrofluorometer with a Xenon Flash lamp excitation source and a photomultiplier tube detector. The parameters used to obtain the steady state emission scan are shown in Table 2.

TABLE 2

Parameters for static fluid scans

| Parameter | Value | Unit |
|---|---|---|
| Excitation | 310 | nm |
| Emission | 400-600 | nm |
| Step Size | 0.5 | nm |
| Delay 1 | 108 | μs |
| Int. Time | 0.3 | μs |
| Averages | 5 | |
| Shots | 10 | |
| Frequency | 200 | Hz |

The nylon bags containing the silica gel were folded and placed into a quartz UV transparent cuvette, and 3 ml of the 0.01 M uranyl solution was added to submerge the sample. The cuvette was placed in the sample holder inside the chamber of the spectrometer with the slits set to the values shown in Table 3, and emission spectra were obtained for each sample in Table 1.

TABLE 3

Spectrometer slit settings.

| Slit Name | Actual value (mm) | Bandpass |
|---|---|---|
| excitation entrance | 3 | 12 |
| excitation exit | 1.25 | 5 |
| emission entrance | 1.25 | 5 |
| emission exit | 1.5 | 6 |

Static Fluid Time Constant

Table 4 shows the spectrometer settings used to measure the kinetics of uranyl transport into the silica gel samples under static fluid conditions.

TABLE 4

Parameters for static fluid scans

| Parameter | Value | Unit |
|---|---|---|
| Excitation | 310 | nm |
| Emission | 496 | nm |
| Duration | 3600 | s |
| Delay | 108 | μs |
| Int. Time | 0.3 | μs |
| Shots | 10 | |
| Frequency | 2 | Hz |

Each silica bag sample was placed into a quartz cuvette containing the 3 ml of the 0.01 M solution. The peak emission wavelength was measured at a frequency of 2 Hz until the intensity reached steady state.

Flow Enhanced Time Constant

Figure 2A:
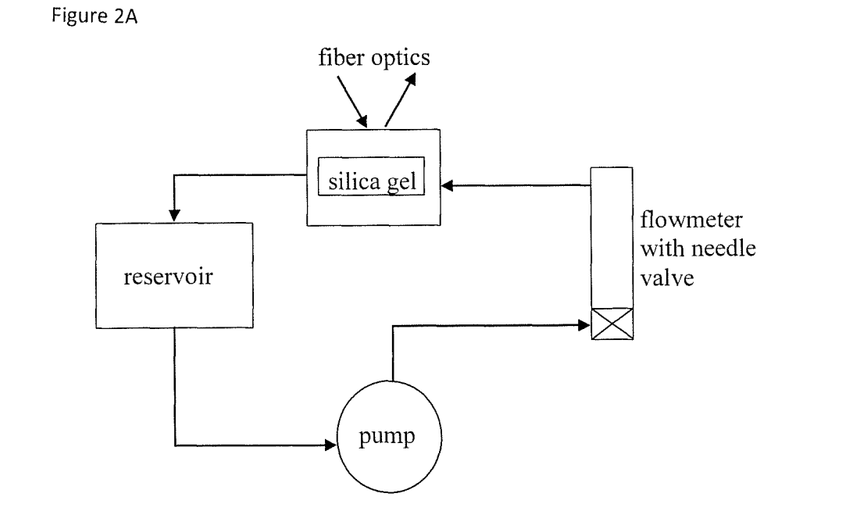
FIGS. 2A and B. A) Schematic of flow system; and B) internal geometry of the silica strainer.
Figure 2B:
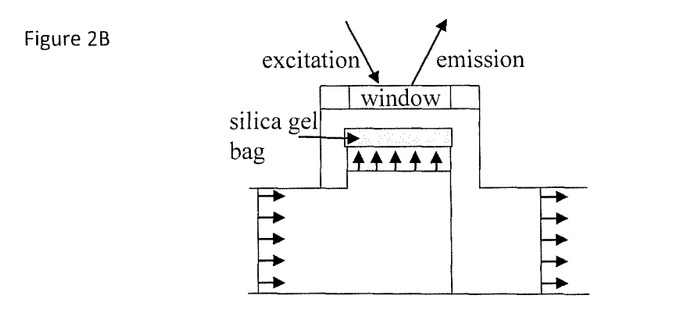

The flow system shown schematically in FIG. 2A was used to measure the kinetics of uranyl transport into the silica gel samples under flow conditions. Fiber optic cables were used to connect the flow system to the spectrofluorometer, and the slits were opened to the values shown in Table 5 to compensate for the signal attenuation caused by the fiber optic connections.

TABLE 5

Spectrometer slit settings for flow enhanced scans

| Slit Name | Actual value (mm) | Bandpass |
| --- | --- | --- |
| excitation entrance | 7 | 28 |
| excitation exit | 7 | 28 |
| emission entrance | 5.5 | 22 |
| emission exit | 3.25 | 13 |

The flow system used ½" ID R-3603 Tygon® tubing, a Danner model 7 utility pump, and a king flow meter with a scale from 0 to 3 gallons per hour (gph). The silica was held in place by a custom-designed flow chamber that included a quartz window through which the excitation and emission light passed.

The fiber optics were aligned perpendicular to the sample as the 0.01 M solution flowed through the silica gel. The flow-enhanced scans were performed with the same solution concentration as the static scans, but the duration, integration time, and frequency of the emission intensity measurements were changed to 150 s, 0.3 s, and 200 Hz respectively because of the much faster adsorption kinetics. The reservoir was filled with 700 mL of solution. The solution was pumped through the silica sample, and the fluorescence intensity was measured as a function of time. The scan began when the pump was turned on, but the zero point for the time constant determination occurred when the leading edge of the water solution first touched the bag. Therefore, this method measured the kinetics of uranyl transport into a dry silica gel to a fully saturated state from the time the solution began to flow through the bag containing the silica gel.

Results and Discussion

Steady-State Emission Spectra

Figure 3:
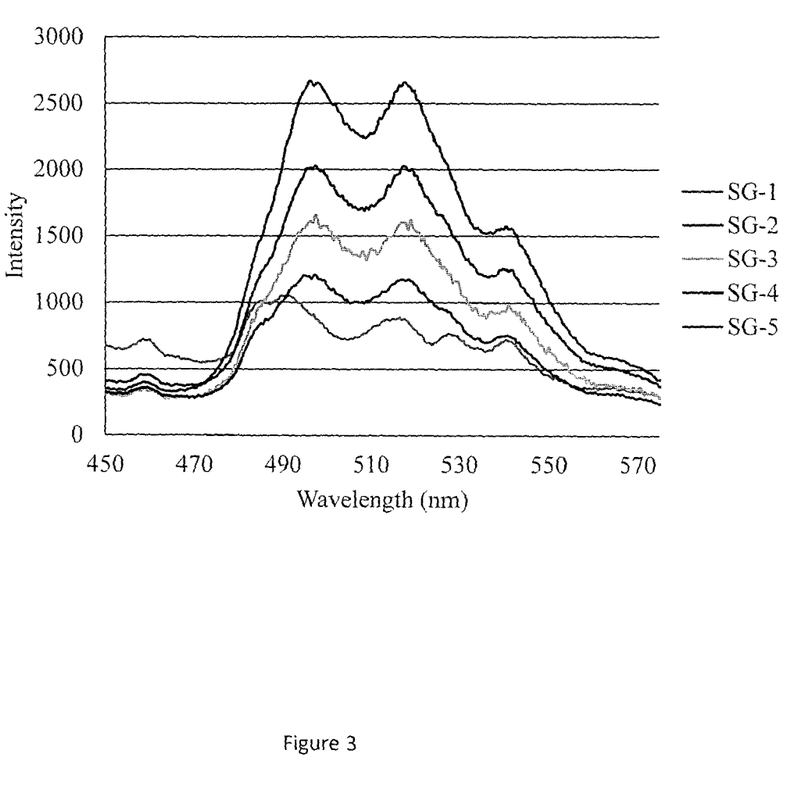
FIG. 3. Fluorescent spectrum of uranyl for silica gels.

The emission spectra for each silica gel in Table 1 are shown in FIG. 3. The spectra were used to determine the peak emission wavelength for the time based scans. Silica gels SG-2 through SG-5 showed three main peaks with the most intense peak at 496 nm. Silica gel SG-1 showed four peaks with the most intense at 491 nm; this resulted in a change of the peak emission wavelength used in the time based scans for this sample (a small blue shift).

Time Constant Results

Figure 4A:
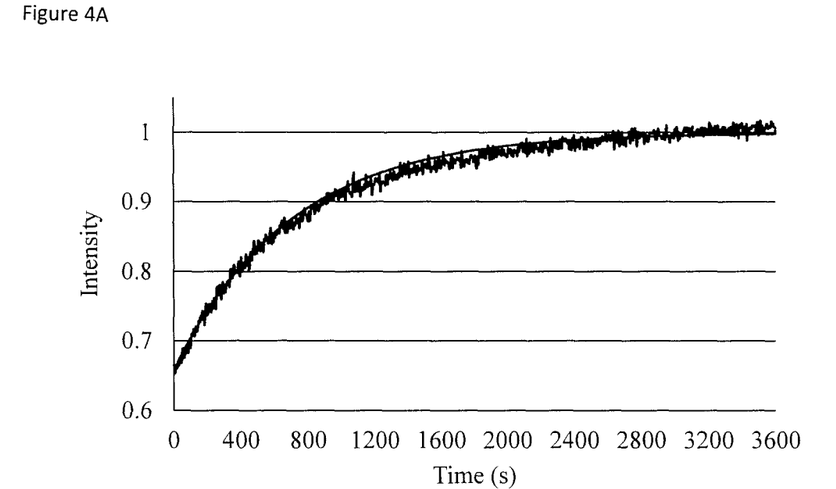
FIGS. 4A and B. A) Normalized florescent intensity vs. time obtained for SG-3 in a quiescent solution; B) normalized florescent intensity vs. time obtained for SG-4 at 1 gph.

FIG. 4A is a normalized plot of the peak emission wavelength intensity as a function of time for silica gel SG-4 in the static uranyl solution. The fluorescence emission intensity increased with time in a manner that can be modeled using a single exponential as shown in Equation 1.

$$I(t) = I_f + (I_o - I_f)e^{\frac{-t}{\tau}} \quad (1)$$

where $I_f$ is the final intensity, $I_o$ is the initial intensity, and T is the time constant. The fit of this curve is shown as the dotted line in FIG. 4A. The data of FIG. 4A shows a large (approximately 50%) enhancement in the uranyl fluorescence intensity caused by the transport and adsorption within the nanoporous silica gel. However, FIG. 4A also shows that it takes a relatively long period of time for this signal enhancement to occur (about 40 minutes to reach steady state). This is the time it takes for the silica to initially wick the water into the pore and for the concentration gradient driven diffusion to reach a steady state. This long time constant is unacceptable for applications requiring rapid detection.

Figure 4B:
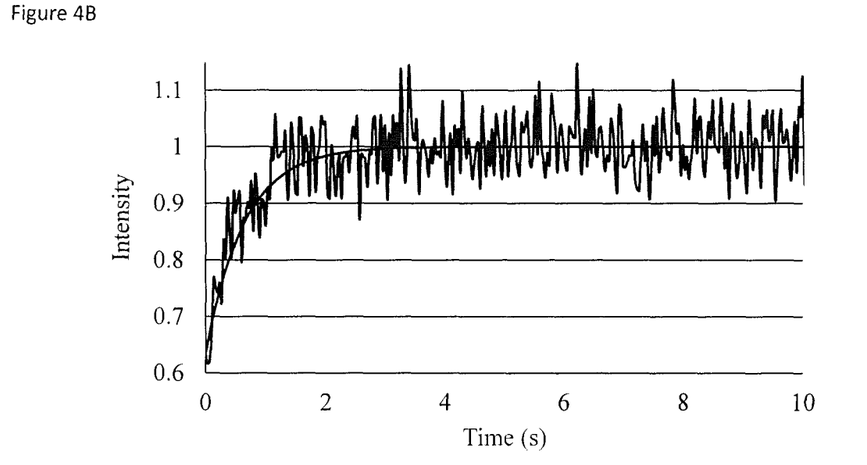
Figure 5A:
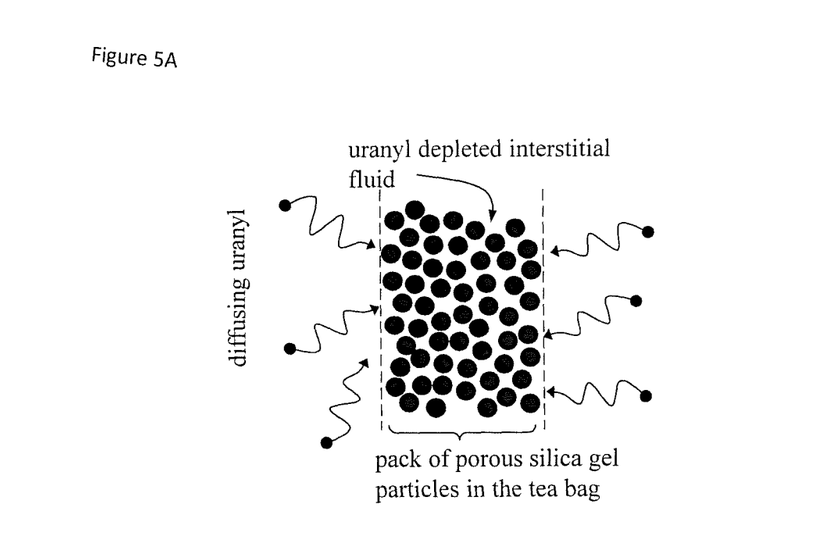
FIGS. 5A and B. A) Schematic representation of uranyl transport into silica gel pack beds in quiescent solution and B) in presence of flow.

FIG. 4B is a normalized plot of the peak emission wavelength intensity as a function of time under flow conditions using SG-3. The magnitude of the fluorescence enhancement under flow conditions was similar (approximately 55%) to the signal enhancement under static conditions, but the time constant is dramatically smaller. Comparing FIGS. 4A and 4B, it can be seen that the fluid flow significantly lowers the time needed for the uranyl fluorescence intensity to reach a plateau. We theorize that the slow saturation rate in the case of quiescent solution is due to the shortage of uranyl in the interstitial fluid inside the tea bags, as shown schematically in FIG. 5A.

Figure 5B:
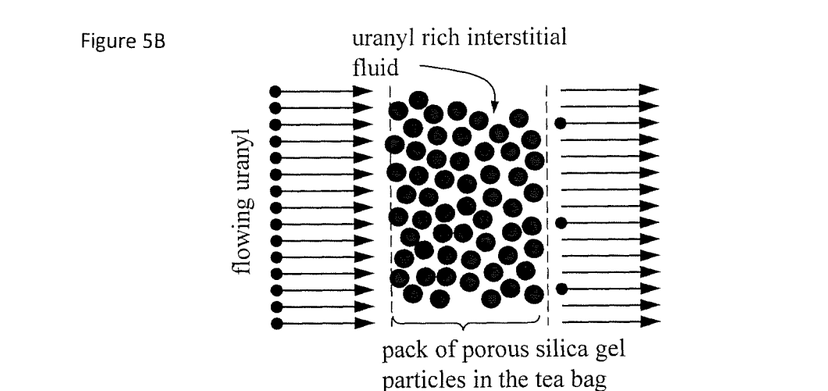

In this case, uranyl transport mechanism is solely due to diffusion in a static fluid driven by the concentration gradient from the bulk concentration to the surface concentration of the silica (Fick's Law). The surface concentration of uranyl is depleted by the uranyl bonding to the silica gel, which forces slow diffusion to take place from the bulk fluid to the surface and then into the pores. The rapid decrease in the saturation time in the presence of flow seems to occur because the fluid flow maintains a constant uranyl concentration around the bed of silica gel particles and eliminates the time delay caused by diffusion (see FIG. 5B).

Figure 6A:
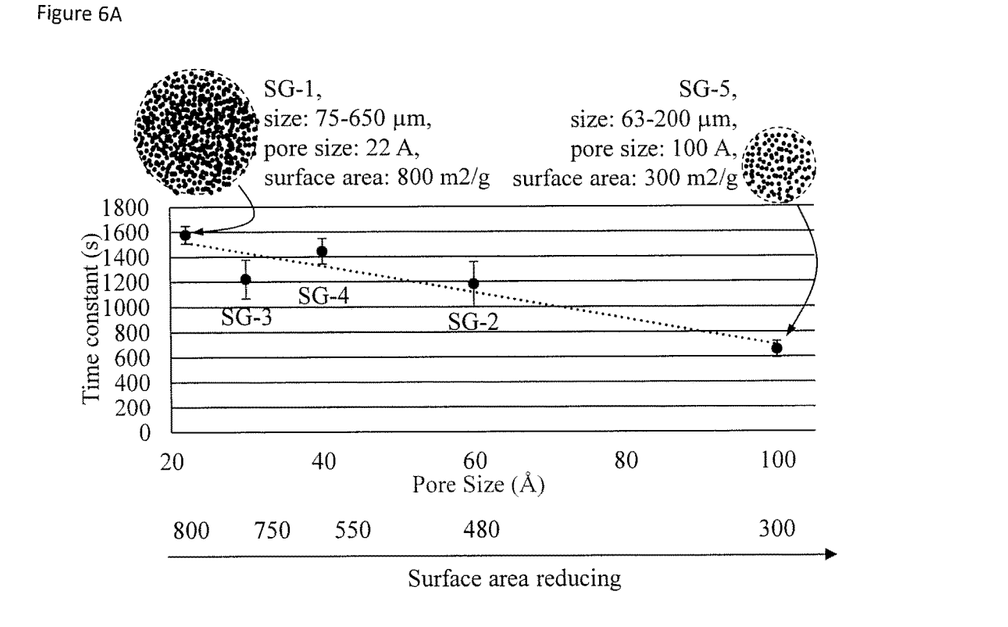
FIGS. 6A and B. A) Time constant in static fluid and B) in presence of flow.

FIG. 6A is a plot of time constant versus pore size in the static fluid. This figure shows that as the pore size increases, the time constant for transport and adsorption from a static fluid decreases. A least square linear fit is obtained for the data in FIG. 6A and is given in Equation 2. Here τ is the time constant and $d_p$ is the nominal pore size of the silica gels. The coefficient of determination $R^2$ was found to be 0.86.

$$\tau = -10.51 d_p + 1745.2 \quad (2)$$

The trend observed in this figure shows that the silica gels with greater nominal pore size (SG-5) has the lowest specific surface area leading perhaps to highest permeability to water. Greater permeability allows the water to penetrate more easily, which carries the uranyl in at a faster rate. The faster penetration causes the uranyl to reach and fill the available bonding sites faster, reducing the time constant.

Figure 6B:
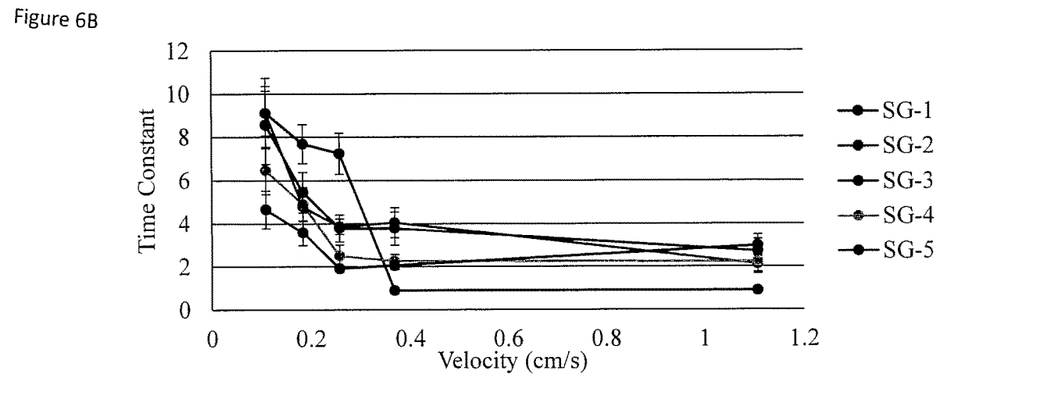

For velocities from 0.36 cm/s down to 0.18 cm/s, the time constant does not appear to have any dependence on the pore size (see FIG. 6B). For the 0.11 cm/s velocity (corresponding to the lowest flow rate used in this study), the time constant does decrease with increasing pore size above 40 Å, similar to the trend shown for the static fluid. Because the silica is initially dry, the water is first wicked into the pores until it becomes saturated. The silica's hydrophilic surface allows the water to rapidly fill the pores compared to the much slower diffusion of the uranyl. The larger pore sizes cause this diffusion to take place at a faster rate. This occurs because the uranyl is removed faster as it reaches the open sites within the pores due to the increased permeability. When the uranyl solution flows through the silica gel particles, some fluid moves around the particles while some fluid flows into the pores. The pores that are connected like a regular granular bed will allow the solution to flow to all sites within the particle. The forced flow through the pores overcomes both the diffusion and permeability affects, which allows the time constant to be reduced by orders of magnitude. FIG. 6B also shows that the there is a critical velocity at approximately 0.36 cm/s. Above the critical velocity, the time constant levels off and become independent of velocity; while below the critical velocity, the time constant increases rapidly toward the static value. The static time constant value at zero velocity is not shown in FIG. 6B as it is orders of magnitude above the scale of that figure. The critical velocity required to achieve the optimum enhancement in adsorption kinetics is approximately the same for all of the pore sizes. The critical velocity is the same for all pore sizes because it is the velocity at which the uranyl transport is no longer being limited by diffusion but is being driven by the fluid flowing into and around the pores. The pore size does have an effect on the kinetics of the uranyl transport from the static fluid.

CONCLUSIONS

In a static fluid, the transport of uranyl ions into nanoporous silica gel takes on the order of one hour to reach saturation as determined by measuring the fluorescence emission intensity as a function of time. In a moving fluid, however, the transport kinetics increases significantly, and the time required to reach saturation is reduced to approximately 2 s at a flow velocity greater than or equal to 0.36 cm/s. Above 0.36 cm/s, the time constant did not depend on the velocity, but at velocities lower than 0.36 cm/s, the time constant increased toward the static fluid case. In a static fluid, the time constant decreased linearly with pore size, but this trend was not observed in a moving fluid at velocities greater than 0.11 cm/s. In a moving fluid, the process of uranyl transport into the pores is no longer controlled by diffusion and permeability. Uranyl transport seems to be dominated by the pressure-driven fluid flow similar to flow through a granular filter. The results indicate that rapid detection and measurement of trace levels of uranyl in water can be achieved by using fluid flow to enhance the transport and adsorption of uranyl onto the available bonding sites within nanoporous silica gel.

REFERENCES

1. Chen C, Pestov D, Nelson J D, Anderson J E, Tepper G. Uranyl Soil Extraction and Fluorescence Enhancement by Nanoporous Silica Gel: pH effects. J Fluoresc. 2010; 21(1):119-24.
2. Pestov D, Chen C, Nelson J D, Anderson J E, Tepper G. Directed fluorescence sensor element for standoff detection of uranium in soil. Sensors Actuators B: Chem. 2009 4/24; 138(1):134-7.
3. Bernhard G, Geipel G, Brendler V, Nitsche H. Speciation of Uranium in Seepage Waters of a Mine Tailing Pile Studies by Time-Resolved Laser-Induced Fluorescence Spectroscopy (TRLFS). RADIOCHIMICA ACTA. 1996; 74:87-91.
4. Table of Regulated Drinking Water Contaminants [Internet]. Available from: www.epa.gov/your-drinking-water/table-regulated-drinking-water-contaminants.
5. Chemical contaminants on DOE lands and selection of contaminant mixtures for subsurface science research.
6. Langmuir D. Uranium solution-mineral equilibria at low temperatures with applications to sedimentary ore deposits. Geochim Cosmochim Acta. 1978 6; 42(6, Part A):547-69.
7. Grossmann K, Arnold T, Ikeda-Ohno A, Steudtner R, Geipel G, Bernhard G. Fluorescence properties of a uranyl(V)-carbonate species[U(V)O$_2$(CO$_3$)$_3$]$_5$ at low temperature. Spectrochimica Acta Part A: Molecular and Biomolecular Spectroscopy. 2009 3; 72(2):449-53.
8. Azenha MEDG, Burrows H D, Formosinho S J, Miguel M G M, Daramanyan A P, Khudyakov I V. On the uranyl ion luminescence in aqueous solutions. J Lumin. 1991 0; 48-49, Part 2:522-6.
9. Parametric Investigation of Laser-Induced Fluorescence of Solid-State Uranyl Compounds. J Phys Chem A. (42): 10502.
10. Jones L H. Systematics in the vibrational spectra of uranyl complexes. Spectrochimica Acta. 1958 February 1958; 10(4):395-403.
11. Lopez M,-Birch D J S. Uranyl photophysics on colloidal silica: an alternative luminescence-enhancing medium for uranyl assay. Analyst. (7):905.
12. Ishibashi K, Sakamaki S, Imasaka T, Ishibashi N. Determination of uranium at ultratrace levels by time-resolved laser fluorimetry. Anal Chim Acta. 1989 1989; 219:181-90.
13. Kenney-Wallace G A, Wilson J P, Farrell J F, Gupta B K. Direct determination of uranyl ion by nanosecond dye-laser spectroscopy. Talanta. 1981 2; 28(2):107-13.
14. Gao B, Yin J, Mao Z, Wang D, Zhang L, Bie L. Synthesis and photoluminescence of blue LED excitable La4Ti9O24:Eu3+ phosphor for red-light emission. Mater Res Bull. 2014 3; 51:185-8.
15. Tran H H, Roddick F A, O'Donnell J A. Comparison of chromatography and desiccant silica gels for the adsorption of metal ions-I. adsorption and kinetics. Water Res. 1999 9; 33(13):2992-3000.
16. Gurgel J M, Filho L S A, Grenier P, Meunier F. Thermal Diffusivity and Adsorption Kinetics of Silica-Gel/Water Adsorption; 7(3):211-9.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of detecting water soluble fluorescent mineral species in an aqueous sample, comprising
   i) directing under pressure the aqueous sample through a solid state porous silica gel in a flow chamber at a controlled flow rate;
   ii) irradiating the solid state porous silica gel with UV light during the step of directing;
   iii) detecting fluorescence emitted from the water soluble fluorescent mineral species bound to the solid state porous silica gel during the step of irradiating,
   iv) comparing a level of fluorescence detected in step iii) with at least one negative control value; and
   v) confirming or indicating that the aqueous sample contains the water soluble fluorescent mineral species when the level of fluorescence detected in step iii) exceeds that of the at least one negative control value.

2. The method of claim 1, wherein the negative control value is a level of fluorescence emitted when a control aqueous sample that does not contain the water soluble fluorescent mineral species is directed through over a control solid state porous silica gel.

3. The method of claim 1, wherein the UV light has a wavelength ranging from 250 to 400 nm.

4. The method of claim 1, wherein the fluorescence has a wavelength ranging from 345 to 600 nm.

5. The method of claim 1, further comprising a step of enhancing a signal to noise ratio of the fluorescence detected in step iii) using an optical filter.

6. The method of claim 1, wherein the water soluble fluorescent mineral species is uranyl.

7. The method of claim 6, wherein the aqueous sample is directed through the solid state porous silica gel at a flow velocity greater than or equal to 0.36 cm/sec.

8. The method of claim 1, further comprising a step of washing the solid state porous silica gel and repeating steps i) v).

9. A portable, hand held device for detecting water soluble fluorescent mineral species in an aqueous sample, comprising
- a chamber for containing solid state porous silica gel;
- a directing device which directs under pressure the aqueous sample through the solid state porous silica gel in the chamber;
- an ultraviolet (UV) excitation source; and
- a fluorometer;
- wherein the device is configured to:
    - i) permit UV light from the UV excitation source to penetrate the solid state porous silica gel, and
    - ii) permit fluorescence emitted from the silica gel to reach the fluorometer.

10. The device of claim 8, further comprising one or more optical filters.

11. The device of claim 8, wherein the directing device is a pump.

12. The device of claim 8, wherein the device directs the aqueous sample through the solid state porous silica gel at a flow velocity greater than or equal to 0.36 cm/sec.

\* \* \* \* \*